United States Patent [19]
Bernhardt

[11] Patent Number: 5,804,430
[45] Date of Patent: Sep. 8, 1998

[54] BOVINE OVARY CELL LINE (FROV) FOR VIRUS REPLICATION

[75] Inventor: Dieter Bernhardt, Cölbe, Germany

[73] Assignee: Behringwerke Aktiengesellschaft, Marburg, Germany

[21] Appl. No.: 208,272

[22] Filed: Mar. 10, 1994

[30] Foreign Application Priority Data

Mar. 13, 1993 [DE] Germany .......... 43 08 092.8

[51] Int. Cl.$^6$ .............. C12N 7/00; C12N 7/01; C12N 7/08; C12N 5/00
[52] U.S. Cl. .................. 435/235.1; 435/240.1; 435/240.2; 435/240.21; 435/237
[58] Field of Search .......... 435/235.1, 240.1, 435/240.2, 237, 240.21

[56] References Cited

U.S. PATENT DOCUMENTS 4,070,453  1/1978  Bordt et al. .

FOREIGN PATENT DOCUMENTS

WO 90/01337  2/1990  WIPO .

OTHER PUBLICATIONS

Puck et al. 1968. Mammalian Cell Growth Proteins . . . PNAS. 59:192–199.
Tsuboi et al. 1992. Growth Activity of Bovoid Herpesvirus I in Bovine Fallicular Docytes. J. Vet. Med. Sci. 54(6):1179–81.
K.S. Chen et al., Adjuvant Enhancement of Humoral Immune Response to Chemically Inactivated Bovine Viral Diarrhea Virus, Canadian Journal of Comparative Medicine, vol. 49, No. 1, pp. 91–94, Jan. 1985.

*Primary Examiner*—James C. Housel
*Assistant Examiner*—N. M. Minnifield
*Attorney, Agent, or Firm*—Finnegan, Henderson, Farabow, Garrett & Dunner, L.L.P.

[57] ABSTRACT

A bovine ovary cell line (FROv), a process for its preparation, and its use for replicating viruses, are described.

4 Claims, No Drawings

BOVINE OVARY CELL LINE (FROV) FOR VIRUS REPLICATION

The invention relates to a bovine ovary cell line (FROv), to a process for its preparation and to its use for replicating viruses.

Living cells are required to produce proteins and viral antigens. It is the state of the art to use diploid cell strains or permanent cell lines for this purpose, provided they are suitable for producing the desired proteins or viral antigens. It is likewise known that diploid cell strains are in general more susceptible to most types of viruses than are permanent cell lines, for which reason they are particularly suitable for replicating a multiplicity of virus types.

However, as compared with diploid cell strains, permanent cell lines have the advantage that their growth is unlimited, i.e. they are immortalized. Over a large number of passages, such permanent cell lines exhibit consistent properties with regard to cell and antigen replication, since, in their case, there is no cell differentiation such as occurs in diploid cell strains. In addition to the limited life span (passage number) of diploid cell strains, a further serious disadvantage of these strains is that the organs from which the diploid cell strains are prepared are not available in adequate quantity nor, necessarily, at any given time. Furthermore, the starting material, i.e. the organs, can be latently contaminated (viruses, mycoplasmas and bacteria), as a consequence of which optimally reproducible antigen production is not ensured. Because of the complexity of problems associated with cell strains, it is understandable that endeavors are being made to employ permanent cell lines for producing viruses and viral antigens, as well as for detecting them (titrations).

Permanent cell lines derived from cattle are also already established, for example MDBK, DBK, Aubeck (Bovine kidney cells) or embryonic thyroid cells. However, the disadvantage of these cell lines is that they only support the replication of a few virus types, such as IBR, $PI_3$, or BAV type 1 or 2, or that they are susceptible to being contaminated with foreign agents and thus cannot be used optimally for producing antigens commercially.

The invention relates to a permanent cell line derived from fetal bovine ovaries, which cell line surprisingly supports the replication of a multiplicity of virus types, such as bovine adenoviruses (BAV): types 1, 3, 4, 5, 6, 7, and 8; parainfluenzavirus (PI): type 3; bovine respiratory syncytial virus (BRSV); bovine herpesviruses: types 1 and 4; equine herpesviruses: type 1; mucosal disease virus: strain Ug59; and bovine parvovirus: strain Haden. This cell line is suitable for use both in producing viral antigens and in detecting viruses.

Establishment of the fetal bovine ovary cell line (FROv)

Starting point:

The ovaries were removed under sterile conditions from an approximately 7 month-old fetus of a Friesian cow at the Marburg slaughterhouse on 14.11.1990. The ovaries were comminuted and dispersed at room temperature into single cells using trypsin. After completing the trypsin treatment, the cell suspension was centrifuged and the cell sediment was resuspended (washed) in Eagle's Minimal Essential Medium (EMEM) and then centrifuged once again.

Cell culture:

The centrifuged, washed cell sediment was taken up, in the ratio 1:300, in EMEM+5% FCS+Antibiotics

| | |
|---|---|
| Neomycin (pure base) | 0.2625 g/l |
| Streptomycin (pure base) | 0.2565 g/l and |
| Penicillin | 0.1212 g/l; |

(NSP) and sown in T50 flasks (from Greiner, Art. No. 690,160).

Cell culture up to 35th passage

The FROv cells were cultivated up to the 35th passage in EMEM+5% FCS+NSP. After achieving dense growth, the cultures were split 1:5 (about 4–6 days). During the cell passages, the culture changed from the mixed cell type (fibroblast and polygonal cells) to a more uniform polygonal cell type.

Cell culture after the 35th passage

The FROv cells were passaged further in three different ways (branches A, B and C):

Branch A of the FROv cells was cultivated with EMEM+ 5% FCS+(NSP) up to the 56th passage. The splitting rate was 1:5 to 1:7.

The 55th passage was deposited with the DSM - Deutsche Sammlung von Mikroorganismen und Zellkulturen GmbH (German Collection of Microorganisms and Cell Cultures), Mascheroder Weg 1 B, 3300 Braunschweig, under the deposition number DSM ACC2051.

From the 56th passage onwards, the species identity test was carried out using the isoenzyme pattern. Result: species, bovine.

From the 35th passage, branch B was replicated using EMEM+2.5% FCS+2.5% horse serum+NSP. FROv cells in the 45th and 51st passages were frozen in liquid $N_2$. Currently the FROv cells of branch B are in the 105th passage. The splitting rate was 1:5 to 1:10.

Branch C of the FROv cells was established from the 51st passage of branch B after storing the cells in liquid $N_2$.

Once the cell suspension had been thawed, the cells were passaged four times. The 55th passage was used to set up a master cell stock (MCS).

For this purpose, the cell suspension was adjusted to $1.8 \times 10^6$ cells/ml and filled up to 1.0 ml in teflon ampoules which were stored in liquid $N_2$. The MCS was tested for sterility and for the absence of mycoplasmas and foreign viruses.

Result: the MCS is sterile and free from mycoplasmas and foreign viruses.

8 days after the MCS had been frozen down, one ampoule was removed from the liquid $N_2$, thawed, and sown in culture medium in a 250 ml culture dish from Greiner, Art. No. 6458170, and then cultivated at 37° C. for further passaging. The FROv cells in branch C were cultivated in EMEM+2.5% FCS+2.5% horse serum+NSP.

The cultivation of the FROv cells given here is by way of example. Cultivation of the cells in other proven media (such as DMEM or TCM 199) and using different sera (calf serum, newborn calf serum or sheep serum) between 1 and 10% is likewise possible.

Examination of virus replication in FROv cells (Branch B)

From the 69th passage onwards, the sensitivity was tested of the FROv cell line, branch B, to the following virus types:

Bovine adenoviruses: Types 1, 3, 4, 5, 6, 7 and 8

Parainfluenzavirus: Type 3

Bovine respiratory syncytial virus (BRSV)

Bovine herpesviruses: Types 1 and 4

Equine herpesviruses: Type 1

Mucosal disease virus (MDV): strain Ug59

Bovine parvovirus: strain Haden

EXAMPLE 1

Densely grown FROv cell cultures (T50 flasks, from Greiner) were changed to EMEM+NSP in order to remove the serum-containing culture medium. The cultures were then infected with the said virus types in serum-free media. In the case of bovine parvovirus, the culture was infected after it was only 70–80% grown. In this infection experiment, three non-infected cultures were carried through as controls.

After 3–10 days, the infected cultures showed, depending on the type of virus, a virus-specific, cytopathic effect. Virus replication had taken place in the FROv cells. The non-infected control cultures, on the other hand, exhibited an intact, unaltered cell lawn.

EXAMPLE 2

In order to monitor virus synthesis in the FROv cell line in the different passages, the FROv cell passages listed in tabular form below were infected with BVD strain Ug59. The procedure for the infection was the same as in Example 1. The table below contains the results.

BVD strain Ug59 replication in the FROv cell line in different passages

| Passage of the FROv cells | Virus crop in days p.i. | Virus titer in FRLu 45 cells/ml of the virus crop |
| --- | --- | --- |
| 69  | 4 | $10^{5.7}$ |
| 70  | 5 | $10^{5.3}$ |
| 72  | 5 | $10^{6.1}$ |
| 75  | 4 | $10^{6.3}$ |
| 75  | 4 | $10^{6.1}$ |
| 75  | 4 | $10^{6.1}$ |
| 75  | 4 | $10^{6.5}$ |
| 78  | 5 | $10^{6.1}$ |
| 80  | 4 | $10^{5.9}$ |
| 81  | 4 | $10^{6.1}$ |
| 83  | 5 | $10^{6.1}$ |
| 88  | 5 | $10^{5.8}$ |
| 95  | 5 | $10^{6.7}$ |
| 100 | 4 | $10^{6.1}$ |
| x*) |   | $10^{6.1}$ |

*)geometric average

For comparison, viral replication of BVD strain Ug59 was monitored in diploid FRLu45 cells, with the values listed below being obtained:

| Passage of the FRLu cells | Virus crop in days p.i. | Virus titer in $\log_{10}$ in FRLu 45 cells/ml of the virus crop |
| --- | --- | --- |
| 5  | 4 | 5.6 |
| 6  | 3 | 6.5 |
| 8  | 5 | 6.7 |
| 10 | 5 | 5.6 |
| 10 | 4 | 5.3 |
| 11 | 3 | 5.8 |
| 11 | 5 | 5.6 |
| x  |   | 5.9 |

Summary of the results: As is evident from the results in the two tables, the quantity of BVD antigen produced (infectivity) is comparable in the two cell systems.

EXAMPLE 3

In order to test the sensitivity of the FROv cells to the virus, BVD strain Ug59 viral crops were titrated in a comparative manner in FRLu 45 cells and FROv cells. The infectivity titres were determined by double titration.

Comparative titration of BVD Ug59 in FROv cells and in FRLu 45 cells

| Virus crop | Titer in $\log_{10}$/ml in FROv cells | Titer in $\log_{10}$/ml in FRLu 45 cells |
| --- | --- | --- |
| 1  | 5.3 | 5.6 |
| 2  | 6.3 | 6.5 |
| 3  | 5.8 | 5.7 |
| 4  | 5.6 | 5.8 |
| 5  | 5.0 | 5.6 |
| 6  | 5.3 | 5.3 |
| 7  | 6.0 | 6.7 |
| 8  | 5.4 | 5.4 |
| 9  | 5.1 | 5.3 |
| 10 | 5.1 | 5.1 |
| 11 | 5.6 | 5.8 |
| 12 | 5.3 | 5.6 |
| 13 | 5.5 | 5.3 |
| 14 | 5.1 | 5.6 |
| 15 | 5.2 | 5.8 |
| 16 | 1.3 | 1.7 |
| x  | 5.2 | 5.4 |

Summary: As these comparative investigations demonstrate, the FROv cell line is only insignificantly less sensitive than the FRLu45 cell for detecting BVD virus.

What is claimed is:

1. A FROv permanent cell line consisting essentially of fetal bovine ovary cells which support the replication of bovine adenoviruses (BAV) types 1, 3, 4, 5, 6, 7, and 8, parainfluenzavirus (PI) type 3, bovine respiratory syncytial virus (BRSV), bovine herpesviruses types 1 and 4, equine herpesviruses type 1, mucosal disease virus strain Ug59 or bovine parvovirus strain Haden, the cell line having the properties of the cell line deposited under the number DSM ACC2051.

2. A permanent cell line consisting essentially of fetal bovine ovary cells, having the growth characteristics of the cell line as claimed in claim 1.

3. A permanent cell line consisting essentially of fetal bovine ovary cells, having the sensitivity to viruses of the cell line as claimed in claim 1.

4. A method for replicating a virus, comprising culturing the virus with a cell line as claimed in claim 1.

* * * * *